United States Patent
Antunes et al.

(10) Patent No.: US 10,911,720 B2
(45) Date of Patent: Feb. 2, 2021

(54) SYSTEM AND METHOD OF ACQUISITION, REGISTRATION AND MULTIMEDIA MANAGEMENT

(71) Applicant: Nuno Antunes, Matosinhos (PT)

(72) Inventors: Nuno Antunes, Matosinhos (PT); Ruben Marques, Matosinhos (PT); José Antunes, Matosinhos (PT)

( * ) Notice: Subject to any disclaimer, the term of this patent is extended or adjusted under 35 U.S.C. 154(b) by 0 days.

(21) Appl. No.: 16/469,169

(22) PCT Filed: Jan. 14, 2018

(86) PCT No.: PCT/IB2018/050226
§ 371 (c)(1),
(2) Date: Jun. 13, 2019

(87) PCT Pub. No.: WO2018/130995
PCT Pub. Date: Jul. 19, 2018

(65) Prior Publication Data
US 2020/0029050 A1      Jan. 23, 2020

(30) Foreign Application Priority Data

Jan. 13, 2017 (PT) .......................................... 109855
Feb. 19, 2017 (GB) .................................. 1702664.2

(51) Int. Cl.
*H04N 7/18* (2006.01)
*A61B 34/00* (2016.01)
(Continued)

(52) U.S. Cl.
CPC ............... *H04N 7/18* (2013.01); *A61B 34/25* (2016.02); *A61B 90/361* (2016.02);
(Continued)

(58) Field of Classification Search
None
See application file for complete search history.

(56) References Cited

U.S. PATENT DOCUMENTS

| 7,370,991 B1 | 5/2008 | Ellis-Fant |
| 2002/0038226 A1 | 3/2002 | Tyus |

(Continued)

FOREIGN PATENT DOCUMENTS

| CN | 203551883 U | 6/2013 |
| CN | 105 487 261 A | 4/2016 |

(Continued)

OTHER PUBLICATIONS

ISR; European Patent Office; NL; Mar. 12, 2018.
Search Report; Portuguese Patent Office; dated Jan. 13, 2017.
Search Report; UK Patent Office; dated Nov. 19, 2019.

*Primary Examiner* — Eileen M Adams
(74) *Attorney, Agent, or Firm* — Patshegen IP LLC; Moshe Pinchas

(57) ABSTRACT

The present invention relates to a system and method of acquisition, registration and multimedia management.
The multimedia system of the present invention comprises a data acquisition module (A), like multimedia glasses, for multimedia data acquisition, a computerized module (B), comprising a data processing unit for controlling the functions, recording, storing, managing and/or sharing, transmitting and/or streaming multimedia data acquired multimedia data, and at least one connection module (C) to connect the multimedia data acquisition module to the computerized module. Optionally, the system may further comprise a multimedia data processing module (D) and an additional connection module (C) to connect to a computerized module (B) and/or to peripheral devices (P).
In a further aspect of the present invention, it is described a multimedia data processing module (D), comprising a unit for data processing, storing, recording, processing, editing and management of multimedia, as well as a multimedia data library (ML).

(Continued)

The present invention lays in the area of multimedia devices and is useful to be applied in areas where there is a need to record activities of manual detailing, in a professional or recreational scope.

15 Claims, 6 Drawing Sheets

(51) Int. Cl.
    *A61B 90/00*     (2016.01)
    *H04N 5/232*     (2006.01)
    *G02B 27/01*     (2006.01)
    *G06F 3/16*     (2006.01)
    *G06K 9/00*     (2006.01)
    *H04N 5/77*     (2006.01)
    *H04R 1/08*     (2006.01)

(52) U.S. Cl.
    CPC ......... *G02B 27/0172* (2013.01); *G06F 3/167* (2013.01); *G06K 9/00255* (2013.01); *H04N 5/23216* (2013.01); *H04N 5/23245* (2013.01); *H04N 5/23299* (2018.08); *H04N 5/772* (2013.01); *H04R 1/08* (2013.01); *A61B 2034/256* (2016.02); *G02B 2027/014* (2013.01); *G02B 2027/0138* (2013.01); *H04R 2499/15* (2013.01)

(56) References Cited

U.S. PATENT DOCUMENTS

| | | |
|---|---|---|
| 2006/0098087 A1 | 5/2006 | Brandt et al. |
| 2013/0042296 A1* | 2/2013 | Hastings ................. G06F 21/10 726/1 |
| 2014/0221785 A1 | 8/2014 | Pacione et al. |
| 2015/0009309 A1 | 1/2015 | Heinrich et al. |
| 2015/0084841 A1 | 3/2015 | Hilkes |
| 2016/0182826 A1* | 6/2016 | Blum ................... H04N 5/2252 348/372 |
| 2016/0210411 A1* | 7/2016 | Mentis ............... A61B 1/00041 |
| 2016/0282628 A1* | 9/2016 | Hilkes ................. G02B 27/017 |
| 2016/0286115 A1* | 9/2016 | Levy ................... H04N 5/2254 |
| 2017/0027651 A1 | 2/2017 | Esterberg |

FOREIGN PATENT DOCUMENTS

| | | |
|---|---|---|
| WO | 2014197109 A3 | 12/2014 |
| WO | 2016/012865 A2 | 1/2016 |

\* cited by examiner

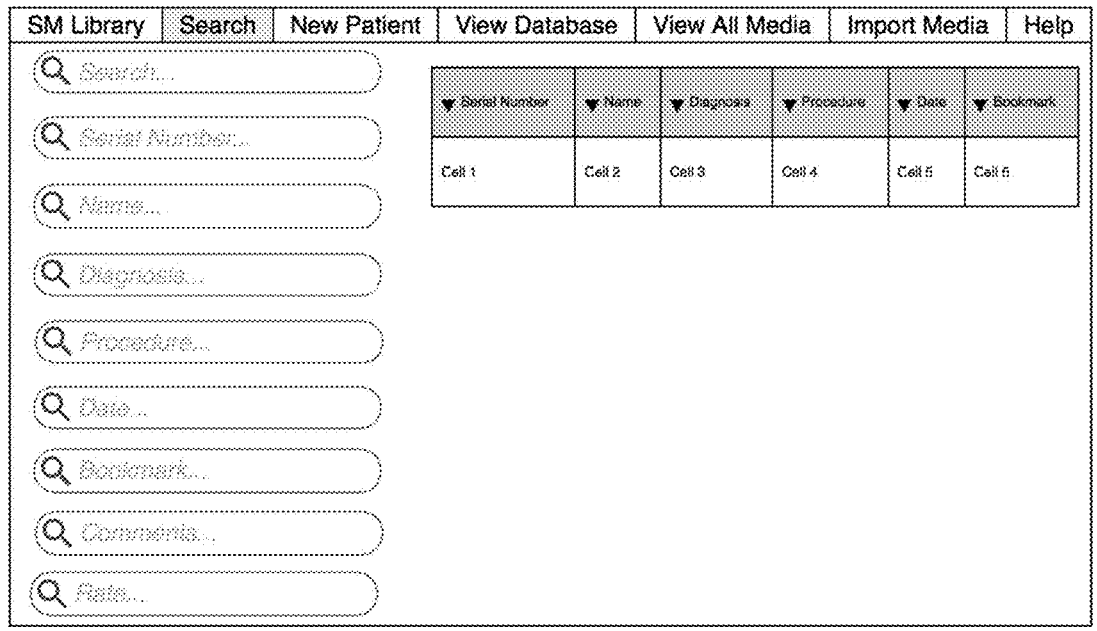
Fig.5.5
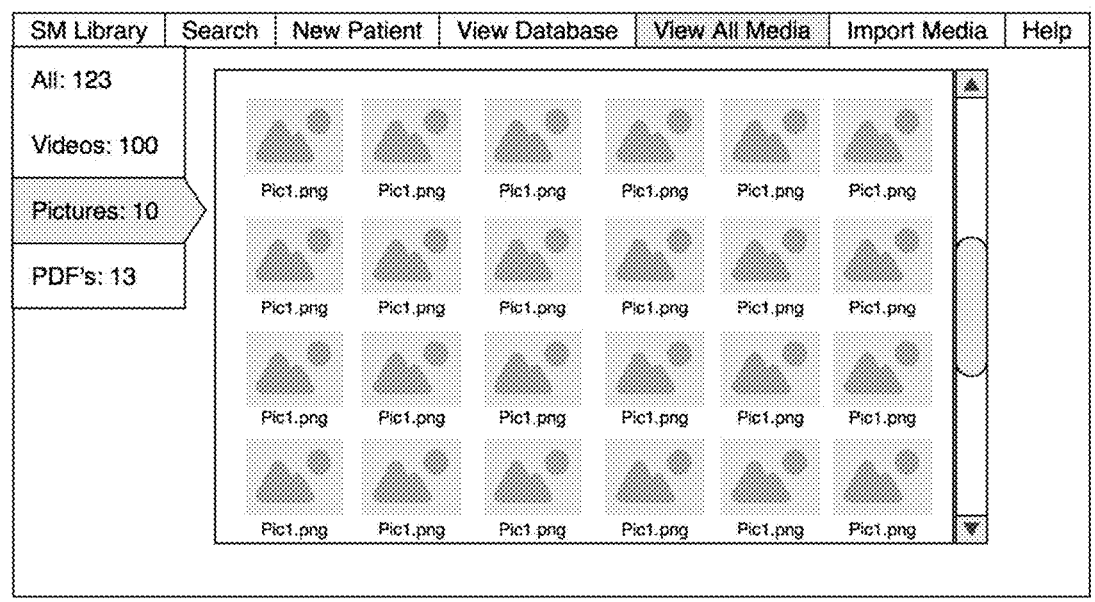
Fig. 5.6

SYSTEM AND METHOD OF ACQUISITION, REGISTRATION AND MULTIMEDIA MANAGEMENT

TECHNICAL DOMAIN

The present invention is related to a system and method of acquisition, registration and multimedia management. Being part of the multimedia devices area, the present invention is useful to be applied in contexts where there is a need to record activities of manual detailing, in a professional or recreational scope, and in which recording is beneficial to the dissemination of art. Emphasis can be made in areas such as medicine, education, civilian security, military, engineering and craft activities. The present invention is thus useful for creating new methods of recording, managing and teaching tools.

BACKGROUND OF THE INVENTION

In the prior art, there are known to exist systems for the acquisition, registration and/or multimedia management, which can be used at a professional or recreational level. Multimedia systems comprising glasses (also known as smart glasses) are already known, such as the ones described in US2016/0286115, WO2014/197109, US2015/0009309 and CN203551883.

Most of these systems include smart glasses with a built-in image capture camera, which may be specific for developing certain functionalities, and a transmitter which transmits the acquired images to a projection device.

US2016/0286115 discloses a multimedia system comprising a camera that captures images from your front field of view, means for transmitting such images to the monitor of a mobile device, which are displayed in a part or window of said monitor and an element that aligns the camera with its frontal field of view, in a manner independent of the angular position of the mobile device or the head or eye of the user, by implementing a counterweight, or some active mechanism. It also mentions the integration of an audio system having an earphones or speakers. Further, it is also not disclosed the form of automatic command, or given by the user, for the camera to start or end capturing images, to focus on the object of interest. In addition, it is disclosed the use of a fisheye type lens and selection of a part of the screen for recording. This choice has the limitation of a resulting variable resolution with the distance to the centre of the image, meaning not all regions of the recorded image are useful for recording details, instead of using a motor. In short, this document only discloses a conceptual device, i.e. does not disclose how these elements are integrated in the device and how to overcome the technical difficulties underlying the manufacture of such glasses, namely regarding the accuracy of the captured images for use in medical field, such as a laparoscopic surgery, the interaction between the surgeon and the sterilized device, etc. In addition, this system provides images captured by a camera to a screen and therefore, the user only sees the displayed images. This unables the disclosed system to be used in the same way of the one of the present invention since the user sees through the screen of the device.

Document WO2014/197109 discloses glasses that project infrared images on a transparent display screen comprising a stereoscopic video camera device including at least two chambers each preferably capturing infrared images from a surrounding environment and a projection system projecting: (i) a first infrared image on a transparent part of the field of view of the left eye, and (ii) a second image on a transparent part of the field of view of the right eye. These glasses allow the user to see the surrounding environment in low light conditions, such as night vision, while maintaining natural vision. For this purpose, cameras that can be aligned through a manual or electromechanical adjustment system are proposed, in order to change the convergence or divergence of the two chambers and thereby provide a three-dimensional effect of varying depth when projecting the images captured on the screens' transparent viewfinder, with an effect that is analogous to the movement of the eyes as they move towards objects at different distances. However, no vertical adjustment for capturing images is mentioned. Also, no mechanism for voice control is provided. Therefore, this system is quite different from the one of the invention and cannot be used for the same purpose.

US2014/221785 (Google Tec. Holdings LLC) discloses a messaging device, which can be smart glasses, that by detection of hand or finger gesture enters in a social media mode, authenticating the user and then converting a spoken message into a social media text message. Therefore, said device comprises a gesture sensing mechanism, a microphone, an application for converting the voice message into text message presented on a display. Said document does not disclose an adjustable video camera controlled by voice for acquisition of multimedia data. Again, the device is quite different from the one of the present invention and cannot be used for the same purpose.

US2013/437854 (GoPro Inc.) discloses a system and a process that generates 3D-images for a video from 2D-images from at least two cameras. Said system only shares with the device of the present invention the feature of being smart glasses having a camera.

Multimedia systems comprising glasses that can be used for medical purposes are disclosed in the documents WO2016/195401 A1, WO2016/190607 A1 and WO2016/182090 A1.

The document WO2016/195401 A1 discloses a system comprising an optical-based Head Mounted Display (HMD) and a set of at least three sensors mounted on the surface or inside of the body of a patient that transmit data to the HMD wirelessly. The HMD is incorporated into glasses which may provide assistance to physicians during surgeries, overlapping the surgeon view of the patient body with the 3D data acquired with the set of sensors.

The document WO2016/190607 A1 discloses a multimedia system comprising glasses with an image display device, an image processing module, a camera for capturing images, a communication unit for transmitting the acquired image to the image processing module, a spectroscopy module in the near infrared (near infrared—NIR) and a communication module for transmitting the image captured by NIR to the image processing module. This system generates images with fluorescence thus allowing the surgeon to superimpose fluorescent images of the area that is being subjected to the operation, in real time, and thus allowing to verify the development of pathologies in real time while performing the surgery.

The document WO2016/182090 discloses a multimedia system comprising a glasses-type terminal, an imaging display unit, a photographic camera, a sensor unit for capturing the user's eyes with respect to the external environment, and a control unit for analysing the user's eyes in order to specify an object.

Nowadays, the most functional multimedia glasses or smart glasses, in terms of image acquisition flexibility, ease of interaction with the user, data transmission and autonomy, are those marketed by Pivothead®. These comprise a video camera located on the nasal bridge, with fixed point of view. The interaction between the user and the device is made by touch and the status indication through LEDs located on the rear face of the glasses frame.

None of these multimedia glasses known in the art tries to actively change the cameras' point of view to match the user's point of view making adjustments in response to the users' voice and allowing to record with precision and accuracy the work performed therein.

The automatic recognition of different recording modes to suit the user's needs, such as a hand recording mode and landscape mode, is also not provided by said smart glasses of the art.

Also, none of the multimedia glasses known in the prior art has a censorship mechanism that detects faces and covers them up in real-time, before the record is made.

In another aspect, none of the existing devices has a mechanism that allows real-time signalling of the area of footage or point of view area.

Additionally, none of the prior art multimedia glasses responds to user's voice or gesture commands to allow adjustments on the point of view of the camera, beginning, stopping, and restarting motion picture capture, still image capture (photography) or adding bookmarks, etc.

Accordingly, it is desirable to develop a system and method of acquisition, registration and management of multimedia data, which may be used in a professional or recreational environment.

SUMMARY OF THE INVENTION

The present invention relates to a system and method of acquisition, registration and multimedia management.

The multimedia system of the present invention comprises a data acquisition module, preferably multimedia glasses, also called smart glasses, for multimedia data acquisition, a computerized module, comprising a data processing unit, for controlling the functions, recording, storing, managing and/or sharing multimedia data acquired and, at least, one connection module for connecting the data acquisition module to the computerized module and sharing, transmitting and/or streaming multimedia data.

Optionally, the multimedia system may further comprise a multimedia data processing module for storing, recording, processing, editing, managing, sharing, transmitting and/or streaming multimedia data and, at least, one additional connection module to connect to a data acquisition module and/or to a computerized module.

The multimedia system of the present invention may further comprise a multimedia data library.

Thus, in a first aspect, the present invention relates to a system of acquisition, registration and multimedia management, according to claim 1.

The use of a data acquisition module (A), a multimedia glasses, with the capacity to change the cameras' point of view to match the user's point of view, in association with a delocalized computerized module (B), with better performance and autonomy when compared with the existing alternatives that integrate the processing and energy storage in the glasses frame, allows highly differentiated multimedia records, supported by higher processing power and autonomy. These records can be then edited, managed, catalogued and stored in a multimedia data processing module (D), leading to better ease of access and consultation of such records and to the creation of an individual and shareable media library.

These glasses that can be operated without a touch interface and with an adjustable point of view provide greater versatility to this device allowing it to have an adequate response to the different demands of the environment. The preferential use of a lighting device as a signalling mechanism of the filming area allows demarcation of the recording area involved.

To allow more functionalities and autonomy without compromising ergonomics, all the computational load and energy storage are done outside the glasses' frame where more volume is available.

The present invention further relates to a multimedia system comprising a data processing module (D) according to claim 2, capable of storing a multimedia library (ML), and/or comprising at least one peripheral device (P), according to claim 3.

The use of a multimedia data processing module, embedded in a computer for instances, enables to do the management, storage and sharing of data on a large scale, with greater ease and better performance than the processing unit.

The existence of a multimedia library allows the user to customize and to have quick and easy access to the stored contents, which are tagged and catalogued in a personalized way.

Finally, the present invention further relates with a method of acquisition, registration and multimedia management, according to claim 15.

The method of acquisition and recording of multimedia data of the present invention allows to capture images from a certain point of view, which can be dynamic, matching with the user's point of view, giving it greater accuracy to the registrations made and minimizing the unintentional loss of multimedia information. In addition, this data can be optionally directed to a computerized module that comprises a data processing unit, for controlling the functions, recording, storing, managing and/or sharing of multimedia data acquired, and/or to a multimedia data processing module, which can allow them to be selectively and objectively stored, managed, edited and shared.

BRIEF DESCRIPTION OF THE FIGURES

FIG. 3: Represents a preferred embodiment of the invention, wherein the multimedia data acquisition module (A) is a multimedia glasses device, in which:

(1) represents the frame of the glasses,
(2) represents a sound based feedback system, such as for example a bone transducer, and
(3) represents one of the temples of the multimedia glasses.

Figure 4:
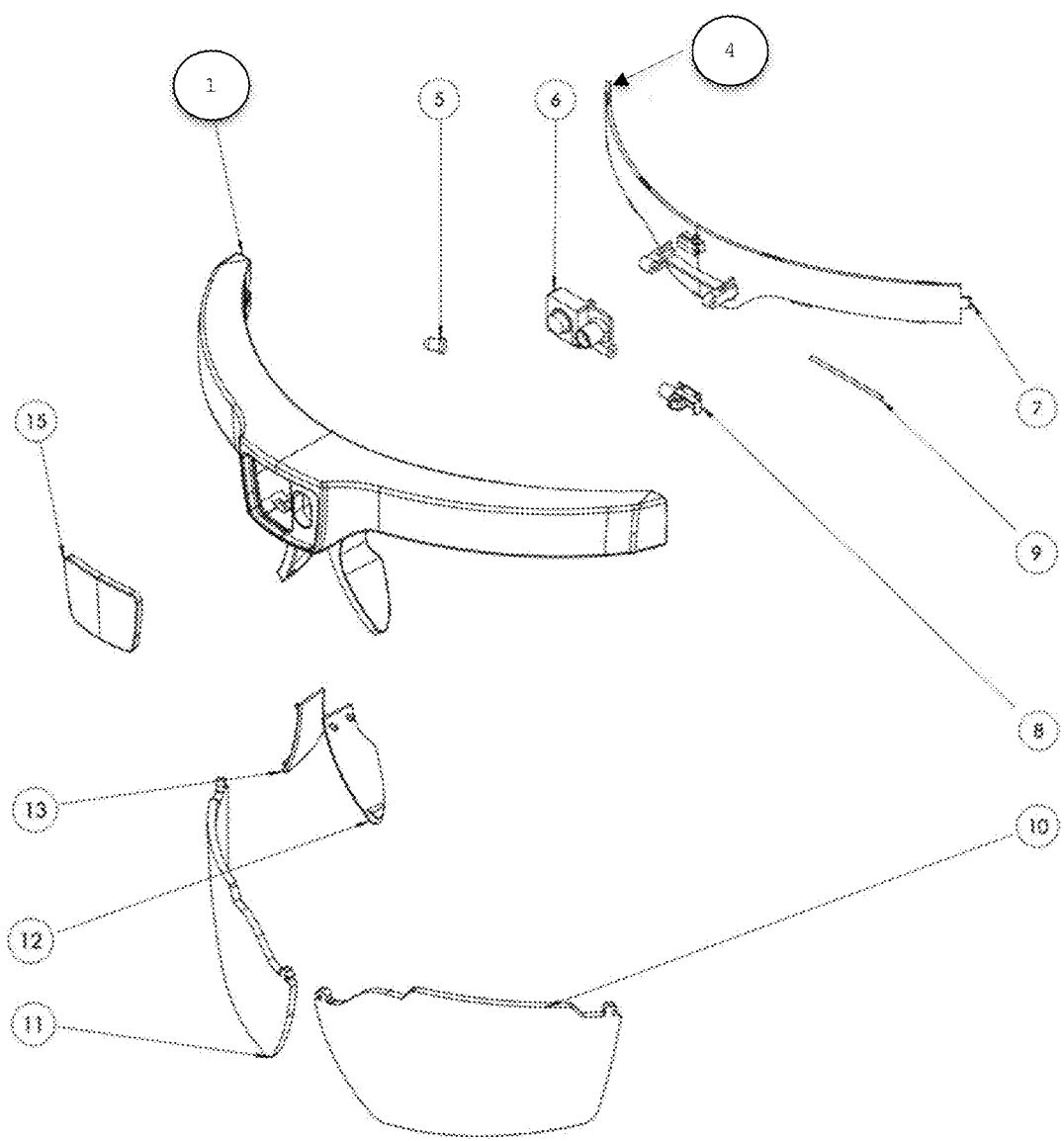
Figure 5:
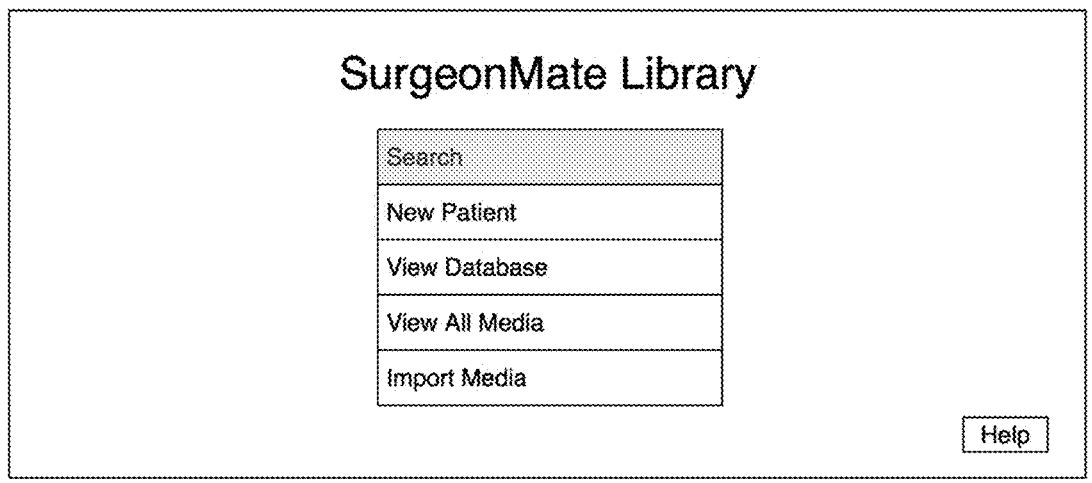
Figure 5:
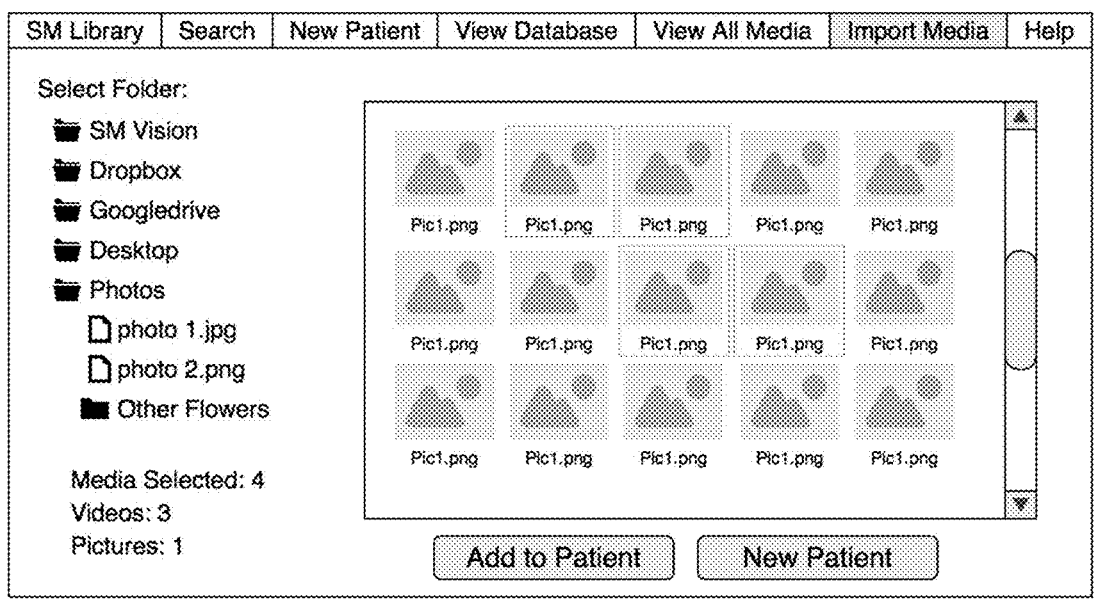

FIG. 4: Represents some of the possible elements of the multimedia glasses, according to a preferred embodiment of the invention, wherein:
1 Represents the frame
4 represents cover of the front set
5 represents a signalling mechanism of the recording status
6 represents a motorized platform with a camera and lightning mechanism that identifies the point of view of the camera.
7 represents the rear wall of the body of the glasses
8 represents the platform-docking motor
9 represents a hinging mechanism coincident with the rotational axis of the platform
10 represents the left lens of the glasses
11 represents the right lens of the glasses
12 represents the left nose pad of the glasses
13 represents the right nose pad of the glasses
14 represents the cover to protect the camera FIG. 5: FIG. 5, is decomposed in FIGS. 5.1 to 5.6, and represents some of the possible interfaces of the multimedia library, according to one of the preferred embodiments of the present invention.

DESCRIPTION OF PREFERRED EMBODIMENTS OF THE INVENTION

Figure 1:
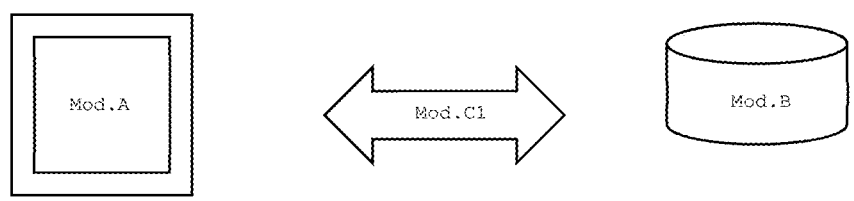
FIG. 1: Schematic representation of the multimedia system of the present invention, wherein (A) represents at least one data acquisition module, (B) represents at least one computerized module and (C1) at least one connection module between the at least one module (A) and the at least one module (B).

In a first aspect, the present invention relates to a multimedia system of acquisition, registration and multimedia management.
1. Multimedia System The multimedia system of the present invention (FIG. 1) comprises, at least one data acquisition module (A), for multimedia data acquisition, at least one computerized module (B), having a data processing unit, for controlling the functions, recording, storing, managing and/or sharing, transmitting and/or streaming multimedia data of multimedia data acquired by at least one module (A) and, at least one connection module (C1), for connecting at least one multimedia data acquisition module (A) to at least one computerized module (B).

Figure 2:
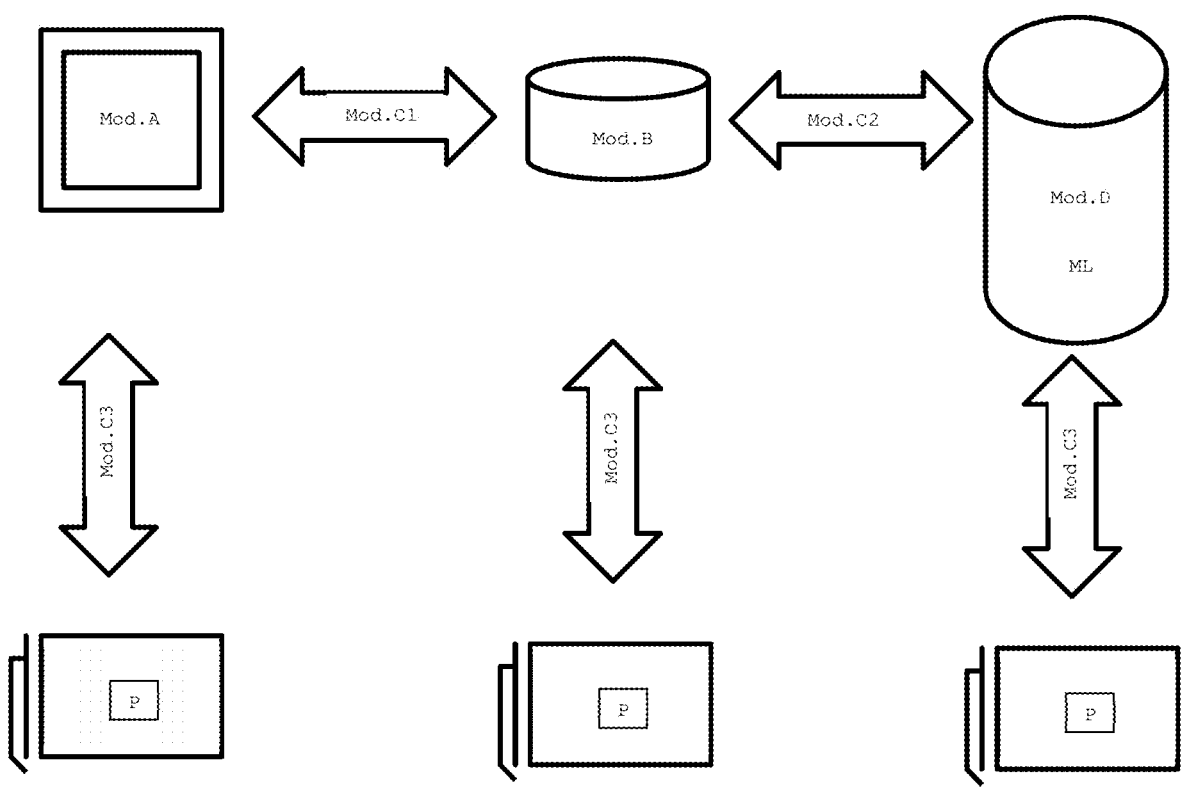
FIG. 2: Schematic representation of a preferred embodiment of the invention, wherein (A) represents a data acquisition module, (B) represents a computerized module, (C1) a module of connection between module (A) and module (B), (D) represents at least one module of multimedia data processing, (C2) represents at least a connection module between the at least one module (B) and the at least one module (D), (P) represents at least one peripheral device, which may be for example equally or differentially, a monitor, a printer, another module (D) and/or a remote control device, and (ML) represents at least a multimedia library.

Optionally, the system may further comprise at least one multimedia data processing module (D) for storing, recording, processing, editing, managing and/or sharing multimedia data and, at least one connection module (C2) to connect at least one multimedia data processing module (D) to at least one computerized module (B), such as in FIG. 2.

Optionally, the system may comprise one or more peripheral devices (P) and at least one connection module (C3), for connection of one or more of said peripheral devices (P) to at least one computerized module (B) and/or to at least one multimedia data processing module (D), also as in FIG. 2.

In the scope of the present invention, peripheral devices (P) may be for example equally or differentially monitors, keyboards, printers, remote controlled devices and/or remote servers.

In a preferred embodiment, the multimedia system of the invention comprises:
  at least one data acquisition module (A), for multimedia data acquisition;
  at least one computerized module (B), having a data processing unit, for controlling the functions, recording, storing, managing and/or sharing, transmitting and/or streaming multimedia data of multimedia data acquired by at least one data acquisition module (A);
  at least one connection module (C1) for connecting at least one multimedia data acquisition module (A) to at least one computerized module (B);
  at least one multimedia data processing module (D) for storing, recording, processing, editing and managing multimedia data, and/or sharing multimedia data;
  at least one connection module (C2) to connect at least one module (D) to at least one computerized module (B); AND/OR
  one or more peripheral devices, such as monitors, keyboards, printers and/or remote control devices;
  at least one additional connection module (C3), for connection of said one or more peripheral devices (P) to at least one computerized module (B), and/or to at least one multimedia data processing module (D) through a connection module (C3).

In a more preferred embodiment, the multimedia system of the invention comprises:
  at least one multimedia glasses of the invention as data acquisition module (A), for multimedia data acquisition; AND/OR
  at least one computerized module (B) of the invention, having a data processing unit, for controlling the functions, recording, storing, managing and/or sharing, transmitting and/or streaming multimedia data of multimedia data acquired by at least one module (A), said module (B) comprises a touch screen and a battery as power source and said data processing unit comprises a computer vision algorithm with the function of blocking and/or preventing the identification of people;
  at least one connection module (C1) for connecting the at least one data acquisition module (A) to at least one computerized module (B) and said connection (C1) is a cable connection with a Y-shape.

In an even more preferred embodiment, the multimedia system of the invention comprises:
  at least one multimedia glasses of the invention as data acquisition module (A), for multimedia data acquisition; AND/OR
  at least one computerized module (B) of the invention, having a data processing unit, for controlling the functions, recording, storing, managing and/or sharing, transmitting and/or streaming multimedia data of multimedia data acquired by at least one data acquisition module (A), said module (B) comprises a touch screen and a battery as power source and said data processing unit comprises a computer vision algorithm with the function of blocking and/or preventing the identification of people;
  at least one connection module (C1) for connecting the at least one multimedia data acquisition module (A) to at least one computerized module (B) and said connection (C1) is a cable connection with a Y-shape;
  at least one multimedia data processing module (D) for storing, recording, processing, editing, managing and/or sharing multimedia data, and at least a data storage unit such as a floppy disk, a DVD, a Blu-Ray, a CD, a ROM, a PROM, an EPROM, an EEPROM and/or FLASH memory, having electronically readable control signals, which are capable of cooperating with a programmable computer system;
  at least one connection module (C2) to connect at least one computerized module (B) to at least one module (D); AND/OR
  one or more peripheral devices, such as monitors, keyboards, printers, remote control devices and/or remote servers;
  at least one connection module (C3), for connection of at least one computerized module (B), and/or at least one multimedia data processing module (D) to at least one or more of said peripheral devices (P).

In a most preferred embodiment, the multimedia system of the invention comprises:
- at least one multimedia glasses of the invention as data acquisition module (A), for multimedia data acquisition;
- at least one computerized module (B) of the invention, having a data processing unit, for controlling the functions, recording, storing, managing and/or sharing, transmitting and/or streaming multimedia data of multimedia data acquired by at least one data acquisition module (A), said module (B) comprises a touch screen and a battery as power source and said data processing unit comprises a computer vision algorithm with the function of blocking and/or preventing the identification of people;
- at least one connection module (C1) for connecting the at least one multimedia data acquisition module (A) to at least one computerized module (B) and said connection (C1) is a cable connection with a Y-shape; AND
- at least one multimedia data processing module (D) for storing, recording, processing, editing, managing and/or sharing multimedia data, and at least a data storage unit such as a floppy disk, a DVD, a Blu-Ray, a CD, a ROM, a PROM, an EPROM, an EEPROM or FLASH memory, having electronically readable control signals, which are capable of cooperating with a programmable computer system;
- at least one connection module (C2) to connect at least one computerized module (B) to at least one module (D); AND/OR
- one or more peripheral devices, such as monitors, keyboards, printers and/or remote control devices;
- at least one connection module (C3), for connection of said one or more peripheral devices (P) to at least one computerized module (B), and/or to at least one multimedia data processing module (D).

Other combinations of the modules of the system described in detail below but not herein explicitly described as the ones above are also comprised in the scope of the invention.

2. Data acquisition module (A)

The data acquisition module (A) is responsible for acquiring multimedia data, such as images and sounds that are transmitted or streamed, in a first instance, to a computerized module (B) for recording. In the present invention data acquisition module (A) is able to capture highly differentiated multimedia records.

In a preferred embodiment of the invention, said data acquisition module (A) is a multimedia glasses device with an integrated camera, speaker and microphone.

Figure 3:
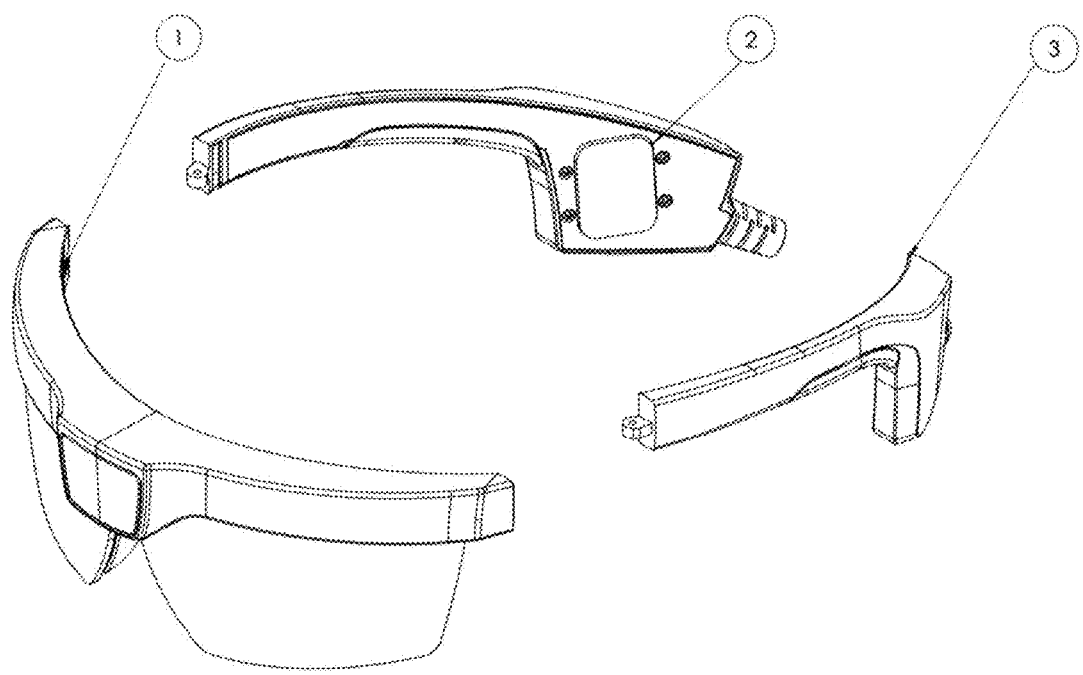

In a more preferred embodiment the data acquisition module (A) is a multimedia glasses according to the present invention, such as for example the ones represented on FIG. 3. These multimedia glasses or smart glasses comprise, besides the frame (1) and lenses (10, 11), at least one camera able to capture static and/or dynamic images, said camera having one or more motors allowing the camera to change its position angle relative to the glasses frame and lenses, an audio system comprising at least one speaker and a microphone, at least one inertial sensor, at least one lighting device for signalling the recording status (5) of one camera and/or for identification of the point of view of the camera, at least one connection module (C1), and optionally a power source.

In an even more preferred embodiment of the invention, the multimedia glasses comprise at least one camera, at least one motor (8) and at least one lighting device placed on a movable platform (6) and said platform is able to adjust the camera position angle manually or automatically when connected to a computerized module (B).

In a most preferred embodiment, the multimedia glasses further comprise audio-system with a bone transducer-type speaker (2).

In a further preferred embodiment, the multimedia glasses also comprise, incorporated in the so mentioned platform or outside of it, at least one light signalling device (5 and 6), for example a LED, for signalling the recording status and/or a lighting device, for identification of the point of view of the camera.

In an even further preferred embodiment, the multimedia glasses also comprise, incorporated in the so mentioned platform or outside of it, an optical mechanism capable of changing the focusing angle of the light from the light signalling device and capable of zooming in and out the camera's field of view.

In an even further preferred embodiment, the multimedia glasses also comprise an anti-fog mechanism with an inner lens that is mounted behind the protection lenses of the glasses. A thin layer of air is contained between the protection lenses and the anti-fog lenses, using an adhesive material on the edge of the lenses for this effect. With such mechanism, the condensation of exhaled water vapour on the protection lenses is delayed or completely prevented, since the anti-fog lenses mounted behind the protections lenses are warmer.

Thus, in the most preferred embodiment, the multimedia glasses of the invention comprise:
- an orientable and motorized platform (6), with a video camera (not shown), for capturing static or dynamic images, a motor (8), which allows to adjust the position of the set, an inertial sensor (not shown) to determine the orientation of the glasses when in use by the respective user, automatically adjusting the camera's point of view to predefined parameters,
- an optical mechanism capable of changing the focusing angle of the light from the light signalling device and capable of zooming in and out the camera's field of view,
- an audio system with a microphone (not shown in FIG. 4), for capturing the user's voice, allowing said user to interact with the smart glasses device via computerized module (B) by giving instructions regarding the recording position, such as starting and stopping the recording mode, turning in and turning off the lightning device that signs the point of view of the camera, and adding voice highlights to the video,
- Lenses with anti-fog mechanism that prevent the condensation of exhaled water vapour on such lenses, allowing the user to have a clear view and,
- at least, one connection module for transmitting the acquired multimedia data to a computerized module (B).

A speaker like mechanism, as part of the audio system, gives a feedback from the computerized module (B) to the user following an instruction given via the microphone and confirms which command will be executed afterwards, preventing accidental and unwanted commands to take place. The audio system, preferably using the microphone and the bone transducer-type speaker (2), can create a way of verbal communication.

2.1 Multimedia Glasses:

The multimedia glasses of the present invention, such as the ones shown in FIG. 3 and already partially mentioned above, acting as data acquisition module (A) are able of acquiring multimedia data and transmitting said data to a computerized module (B).

Preferably built with lightweight materials and ergonomically designed to be used during long-term periods, these glasses incorporate a multimedia, video and audio recording device, preferably into the nasal bridge. Further, these glasses may be at least partially coated with a water resistant or a water barrier film.

Preferably, at the distal end of one of the temples (3) is located a small speaker (2) that, when in contact with the mastoid apophysis of the temporal bone of the wearer, uses preferably the bone conduction pathway to transmit the information from the computerized module (B).

It is also provided the incorporation of an inertial sensor on the multimedia glasses, preferably located at the distal end of one of the temples (3). This sensor aims to identify the position of the user's head, allowing to switch automatically between the available modes of using the multimedia glasses, such as, for example the hand recording mode and the landscape recording mode.

Supporting forms and/or paths of passage for connecting cables may be provided in the glasses' frame, for example to connect said multimedia glasses to a computerized module (B).

Additionally, the multimedia glasses may also comprise a battery in order to provide enough energy to power up, for example, one or more lighting devices, such as LEDs.

The multimedia glasses may further comprise a platform (6) to support or incorporate multimedia data acquisition elements and/or to facilitate the interaction between the users and the computerized module (B).

2.2 Lenses:

The lenses (10, 11) of the multimedia glasses can be customized to allow users who need corrective lenses to use these multimedia glasses (A), not only for multimedia data acquisition, but also for self-protection and for vision deficits correction, during the execution of tasks. The lenses (10, 11) are preferably placed on the fitting locations located on the frame (1) of the multimedia glasses. An anti-fog mechanism with an inner lens may be mounted behind the protection lenses of the glasses. Using an adhesive material on the edge of the inner lenses, a thin layer of air is contained between the protection lenses and the anti-fog lenses.

2.3 Camera:

The video camera is preferably positioned in the nasal bridge, and has the same orientation as the lighting device ideally on a movable platform (6) and is dependent of a motor (8), which provides the capability to change the angle position of the camera, such as vertical tilt and/or.

The position of the camera can be adjusted through voice commands and/or gestures, allowing the user to adjust the point of view of the camera to match his own. These commands make it possible to interact with the computerized module (B) without requiring touch, allowing a variety of instructions to explore all camera functionalities.

2.4 Platform:

In the nasal bridge of the multimedia glasses capturing device there is preferably a platform (6) which is movable due to its incorporation into a motor (8). This platform may also comprise a video camera and at least one lighting device, for example a LED. Preferably located in such platform is the optical mechanism capable of changing the focusing angle of the light from the light signalling device and capable of zooming in and out the camera's field of view.

2.5 Lighting Device:

The multimedia glasses may comprise one or more lighting devices. These may be incorporated in the glasses frame (1) and/or on the platform (6).

Preferably, one of these lighting devices is an LED mounted in the same platform (6) and at the same angle as the camera and has the function to identify the point of view of the camera, i.e. the spotlight indicates the location of the filming/photographing area.

Another preferential embodiment of this invention is the location of a clearly visible signalling light device (5), preferably a LED, in the lateral and front side of the glasses frame (1), which has the function of signalling that the recording mode and multimedia data acquisition is ongoing.

In a most preferential embodiment of the invention, the smart glasses comprise at least one of each of the aforementioned lighting devices.

2.6 Motor:

The motor (8) is preferably located on the nasal bridge of the glasses and coupled to the platform (6) together with the camera and the lighting device and defines the orientation of the multimedia data recording set. This motor confers this module (comprising the platform, camera and lightning device) the ability to move, being controlled through voice and/or gesture instructions, without the need for manual adjustments. However, manual adjustments are also possible.

2.7 Microphone:

Preferably, on the nasal bridge of the multimedia glasses (A), and near the region of the nasal bones, is located a microphone. The microphone may be coated with a suitable film so it can become watertight or moisture resistant. The microphone has the function of transmitting the voice instructions, by the user, to the computerized module in order to be able to adjust the functionalities and/or settings of the glasses (A) to the needs encountered. It also allows the creation of a verbal communication way.

2.8 Speaker:

Preferably the speaker (2) is in contact with the mastoid process of the temporal bone and uses the bone conduction pathway (bone conduction) of sound to transmit information, from the computerized module, to the user. It also facilitates a way of verbal communication.

2.9 Inertial Sensor:

This sensor is preferably mounted on one of the temples (3) of the glasses and allows to identify the position of the head of the user, alternating, preferably automatically, the pre-set modes of use of the data capturing set (platform, camera and lightning device) adjusting the censorship method to be used, whenever applicable, to restrict capturing of sensitive data. It is also used to create the image stabilization system.

2.10 Connection Module (C1):

The data acquisition module (A) needs to comprise, at least, one form of connection to a data processor, which allows, at least, receiving, storing, recording, managing, sharing, transmitting and/or streaming said received multimedia data.

This connection can be made through cables, Wi-Fi, Bluetooth, infrared and/or any other form of connection that allows sending, sharing, transmitting and/or streaming the multimedia data acquired by data acquisition module (A) to a data processor, for example a data processing unit of a computerized module (B).

In a preferred embodiment of the present invention, the connection module (C) comprises a connection (C1) to a computerized module (B).

In a more preferred embodiment, such computerized module (B) is the computerized module (B) of the present invention.

The connection between the glasses (A) and the computerized module (B) can be carried out through cables to increase connection security and data privacy. The electronic cables pass preferably through the temples (3) of the glasses.

Preferably, two sets of cables leave the frame, one at the end of each temple (3) of the glasses, being reunited in a Y-shaped manner (so-called Y-shaped cable connection) at a fixed distance from the exit of the temples (3). Furthermore, the user can adjust a sliding device across the Y-shaped cable to further reduce the distance at which the two cables exiting the temples contact each other, offering the advantage of increasing the safety of holding the glasses on the user's head during sudden movements or positions that favour the natural drop of the glasses.

3. Computerized Module (B)

3.1 Processing Unit:

The computerized module (B) comprises a data processing unit for controlling the functions of at least one data acquisition module (A), recording, storing, managing and/or sharing, transmitting and/or streaming multimedia data acquired by a data acquisition module (A), a touch screen and/or keyboard, and a power source and/or connection to a power source.

Said computerized module (B) is capable of reacting to the instructions provided by the user via data acquisition module (A) and/or via its own touch screen and/or keyboard and it can be controlled remotely by an authenticated person via a network, such as intranet and/or internet.

Computerized module (B) also comprises at least one connection module (C1), for connecting to at least one multimedia data acquisition module (A).

Computerized module (B) may further comprise at least one connection module (C2) for connecting said computerized module (B) to at least one multimedia data processing module (D), and/or at least one connection module (C3) for connecting the computerized module (B) to at least one or more peripherals devices (P).

The computerized module (B) comprises preferably a battery as a power source, which supplies power to said computerized module (B) and also preferably to data acquisition module (A). This battery can be rechargeable and can also supply power while connected to a power supply socket in order to make the computerized module (B) portable or transportable.

The data processing unit of the computerized module (B) allows to control the functions of at least one data acquisition module (A), in particular, to start, stop and restart of motion picture capture, still image capture (photography) or bookmarking of points of interest.

In a preferred embodiment of the invention, the data processing unit of the computerized module (B) includes a computer vision algorithm, such as for example a facial detection system, with the function of preventing or blocking the identification of people, in order to avoid capturing sensitive data related to identifiable people.

3.2 Screen:

The computerized module (B) may also comprise a screen, which has the preferred function of creating a manual interface mode between the user and its data processing unit, as well as to enable the viewing of captured multimedia content.

This screen is preferably tactile or touch screen and may be located on the front face of the computerized module (B). In another embodiment of the invention the screen is not tactile and in this alternative, the input of instructions by the user can be achieved through a keyboard, which may be incorporated in the computerized module (B) or that instruction input can be performed remotely.

In another preferred embodiment, the computerized module (B) comprises a touch screen and also the possibility of being operated remotely.

The computerized module (B) can further be coated by an encasement or by a film, which is preferably water resistant or watertight. The computerized module (B) can further comprise a seal for security and/or privacy purposes.

3.3 Connection Modules (C1)(C2)(C3):

The computerized module (B) needs to comprise, at least, one form of connection to a data acquisition module (A), for example a connection (C1), and to at least a multimedia data processing module (D), for example a (C2) allowing said multimedia data processing module (D) to store, record, manage, share, transmit and/or streaming said received multimedia data. Further, it may also comprise a connection module, for example a (C3), for connection to at least one peripheral (P) device.

The connection type (C1) has already been described above. The connection type (C2) and (C3), such as the connection type (C1), may be performed by means of cables, Wi-Fi, Bluetooth, infrared and/or any other type of connection.

Connection type C2 enables the computerized module (B) to send the multimedia data acquired by at least a data acquisition module (A) and contained in at least a computerized module (B) to at least one multimedia data processing module (D) and/or to at least one peripheral (P) device.

Connection module (C3) enables computerized module (B) to send and/or receive, share, transmit and/or streaming multimedia data to at least one multimedia data processing module (D) and/or to at least one peripheral (P) device.

Optionally, computerized module (B) may comprise one or more connections (C3) to one or more peripheral devices (P), such as external computers, monitors, printers, and/or other multimedia data processing modules (D).

Preferably, the connections type (C2) and (C3) are made by wireless transmission, such as Wi-Fi, infrared and/or Bluetooth.

4. Connection Module (C)

The system of the present invention needs to comprise, at least, one form of connection from at least one data acquisition module (A) to at least one computerized module (B), for example, a connection of the type (C1).

Preferably, the system of the present invention comprises two types of connection: (i) one connection of the type (C1), which allows transmission of the multimedia data between a data acquisition module (A) and a computerized module (B), and (ii) another connection of the type (C2), for sharing, transmitting and/or streaming multimedia data between a computerized module (B) and a multimedia processing module (D).

Optionally, the system of the present invention may further comprise another type of connection (iii), for example a connection of the type (C3), which enables to share, transmit and/or streaming multimedia data between any of said modules (A, B or D) to at least one or more peripheral devices (P), such as, for example, external monitors, remote control devices, printers, remote servers, etc.

In the scope of the present invention, transmitting multimedia data also means receiving, sending, sharing and/or streaming said data.

These connections can be made via cables, Wi-Fi, Bluetooth, infrared or any other form of connection that allows to send and receive, transmit, share and/or streaming multimedia data between said modules.

5. Multimedia Data Processing Module (D)

The processing module (D) comprises a data processing unit for storing, recording, processing, editing, managing and/or sharing multimedia data. In the scope of the present invention, said multimedia data processing module (D) may be for example, a remote server, a computer, a portable or transportable Computer, a Laptop, a Notebook, a Tablet or any other device capable of storing, processing, managing, editing and/or sharing multimedia data.

Multimedia data processing module (D) also comprises at least, one form of connection (C2) to a computerized module (B) for connecting said multimedia data processing module (D) to a at least one computerized module (B) and/or at least one connection module (C3) for connecting said multimedia data processing module (D) to at least one peripheral device (P) for example to a monitor, a keyboard, a remote control device, a printer, a remote server, etc.

Additionally, the multimedia data processing module (D) comprises a computer program for performing a method of acquisition, registration and/or multimedia management comprising the following steps:
a) Acquisition of multimedia data from at least one data acquisition module (A),
b) Sending, transmitting and/or streaming the data acquired by at least one module (A) to at least one computerized module (B) through a connection module (C1),
c) Sending, sharing, transmitting and/or streaming the data from at least one computerized module (B) to at least one processing module (D), through a connection module (C2),
d) Storing, registering, processing, editing and/or managing received multimedia data in at least one processing module (D) and/or a data storage unit such as a floppy disk, a DVD, a Blu-Ray, a CD, a ROM, a PROM, an EPROM, an EEPROM or a FLASH memory having electronically readable control signals, which are capable of cooperating with a programmable computer system,
e) Optionally sharing, transmitting and/or streaming said multimedia data to at least one peripheral device (P) through a connection module (C3) and/or to at least one other processing module (D);
f) Optionally creating a multimedia data library (ML).

The multimedia data processing module (D) may also comprise at least one data storage unit such as a floppy disk, a DVD, a Blu-Ray, a CD, a ROM, a PROM, an EPROM, an EEPROM and/or a FLASH memory having electronically readable control signals, which are capable of cooperating with a programmable computer system.

Optionally, the multimedia data processing module (D) further comprises a multimedia data library (ML) with multimedia data acquired preferentially by at least one data acquisition module (A).

6. Multimedia Data Library (ML)

The multimedia data library (ML) of the present invention comprises multimedia data, which may be in conventional support and/or in digital support, as for example recorded in a data storage unit, such as a floppy disk, a DVD, a Blu-Ray, a CD, a ROM, a PROM, an EPROM, an EEPROM and/or FLASH memory, susceptible to be read electronically by a reader and/or multimedia data processor, having such multimedia data been preferably obtained from recording multimedia events with a multimedia data acquisition module (A), preferably the multimedia glasses of the present invention.

In a preferred embodiment of the invention, the multimedia data were subjected to prevention and/or blocking of the identification of the intervening subjects, identification blocking including prevention and/or blocking of facial identification, prevention and/or blocking of voice identification, among others.

In another preferred embodiment the multimedia data library (ML) is security protected by any known means, for example by user password and/or server password and/or pseudo-anonymizations of the metadata introduced on the library, in order to have restricted access.

Notwithstanding, it is possible to share the total contends or only selected parts of the multimedia data library (ML) with one or more members of a network or with a predefined community with accessing rights to said library (ML).

7. Method of Acquisition, Registration and Multimedia Management

The method of acquisition, registration and/or multimedia management of the present invention comprises the following steps:
a) Acquisition of multimedia data from at least one module (A) of the type multimedia glasses, which is controlled by at least one computerized module (B),
b) Sending, transmitting and/or streaming, transmitting and/or streaming the data acquired by at least one module (A) to at least one computerized module (B) through at least a connection module (C1),
c) Optionally sending, sharing, transmitting and/or streaming the data from at least one computerized module (B) to at least one processing module (D), via at least one connection module (C2),
d) Optionally, registering, processing, editing and/or managing received multimedia data in at least one processing module (D) and/or a data storage unit such as a floppy disk, a DVD, a Blu-Ray, a CD, a ROM, a PROM, an EPROM, an EEPROM or a FLASH memory having electronically readable control signals, which are capable of cooperating with a programmable computer system,
e) Optionally sharing, transmitting and/or streaming said multimedia data from at least one module (D) to at least one peripheral device (P) and/or to at least one other processing module (D) through a connection module (C3), and/or
f) Optionally creating a multimedia library (ML).

In a preferred embodiment of the present invention the data acquisition module (A) is a multimedia glasses as described in section 2.

In another preferred embodiment, the computerized module (B) is as the one as described in section 3.

In another preferred embodiment of the invention, the connection module (C1), (C2) and/or (C3) are as described in section 4.

In another preferred embodiment, the multimedia data processing module (D) is as the one as described in section 5.

In another preferred embodiment, the multimedia data library (ML) is as the one described in section 6.

In a most preferred embodiment, the method of the present invention comprises a combination of two or more of the above preferred embodiments.

EXAMPLES

Example 1: Method for Multimedia Data Acquisition and Registration During a Laparoscopy In this example, the multimedia system of the invention comprises a smart glasses unit as data acquisition module (A) as shown in FIG. 3, a computerized module (B) and a multimedia data processing module (D).

With the data acquisition module (A) mounted on the head, the user can:
1. Start the recording by using
    a. voice commands, starting with a predefined and personalised activation expression, followed by the proper command that indicates the intention to start the recording, AND/OR
    b. the touchscreen interface, located in the computerized module (B);
2. Change the recording pre-set mode, if it is already active, for example, during the laparotomy procedure, simply by having the head in a neutral position, looking forward to the laparoscopy screen, the computerized module (B) is able to acquire information about the inclination of the head, using the inertial sensor mounted on the data acquisition module (A), and, after a configurable time, changes the orientation of the camera to match the predictable surgeon's point of view;
3. Add bookmarks while recording, so that the processing module (D) can automatically identify the points of interest of the recording data. These bookmarks can be added with voice commands, using a predefined and personalised activation expression, followed by the proper command that indicates the intention to add a bookmark and its respective number;
4. Audio feedback, from the computerized module (B), is given to the user every time a voice command is activated preventing misunderstandings after a command, by giving the user information about the command that will take place following the feedback.

During a laparoscopy procedure, the area of interest that is effectively registered has to contain the laparoscopy monitor (P). The borders of the image may be darkened or completely eliminated using a digital zoom that only contains the monitor (P).

The computer vision algorithm, via inertial sensor, may still help censoring areas with sensible data, for example faces, when the user relaxes his neck muscles and unintentionally changes the point of view of the camera.

When recording in environments that contain sensible data, as it is the case of the present example, the user must end the recording with a voice command using a predefined and personalised activation code or expression, followed by the proper command that indicates the intention to end the recording.

Example 2: Method for Multimedia Data Acquisition and Registration During a Laparotomy In this example, the multimedia system comprises the same modules as mentioned above.

With the data acquisition module (A) placed on the head, the user can:
1. Start the recording by using either
    a. voice commands, through a predefined and personalised activation sentence followed by the command that starts the recording, AND/OR
    b. by using the touchscreen interface in the computerized module (B),
2. Change the recording pre-set mode if active, for example during a laparoscopy simply by leaning his head down, towards the operating field. Through the inertial sensor assembled in the glasses, the computerized module (B) will acquire the head's orientation and after a configurable amount of time, for example 5 seconds, the camera will tilt downwards, moving with the surgeon's look;
3. Add bookmarks to the video recording, which can later be read by a video editor of a multimedia data processing module (D), will make easier to locate the most relevant parts on the recorded footage. These markers can be added with voice commands, using a predefined and personalised activation sentence followed by the specific command that indicates the intention of creating a bookmark with an associated number;
4. Audio feedback, from the computerized module (B), is given to the user every time a voice command is activated preventing misunderstandings after a command, giving the user information about the command that will take place following the feedback.

In this operating pre-set mode, it is possible that there are faces in the recording area of the camera. When this happens, the facial detection algorithm will censor them, to protect the privacy of those involved in the surgery and the staff on the operating room. To finish the recording, the surgeon can issue a voice command with a predefined and personalised activation code or expression followed by the command to stop the recording.

Example 3: Method for Multimedia Data Acquisition and Registration During Artisan Work, Repairs, or Other Manual Labour With the glasses placed on the user's head, the user can:
1. Begin the recording by:
    a. using voice commands, using a predefined and personalised activation sentence followed by the command to begin the recording, AND/OR
    b. using the touchscreen interface located in the computerized module (B),
2. Change the orientation of the camera, incrementally, to bring the working area into focus by:
    a. voice commands, using a predefined and personalised activation sentence followed by the command that indicates the movement desired, AND/OR
    b. using the touchscreen interface located in the computerized module (B), The user can have feedback on the area that is focused by looking at the screen located in the computerized module (B) or by acknowledging the area illuminated by the lighting mechanism.
3. Add bookmarks to the video recording, which can be read at a later stage by a video editor, to make it easier to locate in time relevant parts of the video. These markers can be inserted by:
    a. voice commands, using a predefined and personalised activation code or expression followed by the specific command, AND/OR
    b. using the touchscreen interface in the computerized module (B).

The user should end his recording using a voice command, a predefined and personalised activation sentence followed by the command, or by using the touchscreen interface.

Example 4: Method to Wirelessly Transmit Content to Remote Locations (Streaming), Similar to the Previous Examples The user can wirelessly transmit content while recording by:
1. using a wireless network created and managed by the computerized module (B), perfect for conferences where content is shared in real time in a local network. To use this functionality the user must know the name and password of the network, located in the screen of the computerized module (B),

AND/OR 2. transmitting over the internet to remote locations. To enable this feature, the user must contact the network's administrator where the computerized module (B) is connected to, and prepare a public address to share with the interested people, so that they can visualize the contents in any multimedia client prepared to read streamed content. Optionally, the user may need to authenticate in order to view the broadcasted content.

Example 5: Method to Create, Edit and Manage a Multimedia Data Library (ML)

The video processing software (FIG. 5.4) enables the user to select the most relevant segments of the recording, a process eased by the bookmarks inserted during the recording, and saves them along with the metadata inserted in a pseudo-anonymized and encrypted format only accessible after authentication.

The user begins by authenticating with a password and ideally, with a two-factor authentication using a code received in his mobile phone. If used by a doctor to record medical surgeries, with the card reader, the user can also authenticate with his medical certificate.

With the computerized module (B) connected to the multimedia data processing module (D), the user can, after authentication:

1. Browse the library of records created by:
a. Searching for records by one or more of the associated metadata (FIG. 5.5), AND/OR
b. Querying a table that organizes all metadata stored so far,
2. Import a new record into the library (FIG. 5.2), specifying the metadata associated with it (FIG. 5.3). In the scope of surgical registration, these metadata can include the name of the patient, the surgical procedure, the date of surgery, the location, observations, etc.

Example 6: Multimedia System with the Ideal Smart Glasses System for Use in an Operating Room A wearable head mounted device comprising a glasses frame (FIG. 3) hereinafter (module A), that is connected to a computerized module (module B), through a pair of cable assemblies, joined together in a Y-shape, in the back of the user's head, for added stability and safety while using the device. The following subparagraphs refer to particular features present in the glasses:

6.1: Module A has a camera located in the nasal bridge mounted in a rotatable platform (6).

6.2: Module A has an LED light mounted on the same platform (6) as the camera, to illuminate its field of view and give a feedback to the user on the area that is being recorded.

6.3: Module A has a motorized (8) system behind the platform on which the camera and light are mounted, to rotate it vertically and horizontally.

6.4: Module A has an optical mechanism to change the focusing angle of the light from the LED and to zoom in and out the field of view of the camera.

6.5: Module A has a status LED (5) mounted in the front face of the body of the frame, to the left or right ends, to give feedback to other people on the recording status of the device.

6.6: Module A has a bone conducting transducer (BCT) positioned in the back side of the right arm of the frame (2), behind the right ear, making contact with the mastoid process of the temporal bone. This frees the external auditory canal, while retaining the privacy not achievable using regular speakers. With this mechanism, while using this device, there is no interference with the communication inside the operating room.

6.7: Module A has a microphone mounted to the right or left of the camera, LED and motor assembly, so that the user can record audio and give voice commands to the device.

6.8: Module A has an inertial sensor positioned in the front, next to the microphone, to detect the inclination of the glasses frame, and consequently the inclination of the user's head.

6.9: Module A has protections lenses (10, 11) in front of the eyes of the user. If the user needs eyesight correction, these lenses include it in themselves.

6.10: Module A has anti-fog lenses mounted behind the protection lenses.

6.11: Module B has a touchscreen that the user can use to interact with the device, defining settings, start and stop recording, previewing, etc.

6.12: Module B has a battery that powers all the systems of the device, for up to 12 hours.

6.13: Module B has a processing unit responsible for the storage and processing of the recorded media and controlling the many hardware subsystems of the device.

6.14: Module B can connect to other devices using Wi-Fi networks and/or using Bluetooth technology, in order to stream the media being record.

Example 7: Multimedia System with Smart Lasses that Use an External Power Supply Having the same general features as described in Example 6, the device is powered by an electric cable that is connected to module B and to a power source such as an electrical plug or generator, indefinitely extending the normal autonomy of the device, as long as power is available at the source.

Example 8: Multimedia System with Smart Glasses with Reduced Volume Carried on the Waist Having the same description as in Example 6, the processing unit of module B is moved to module A to one of the arms of the frame, the touch screen of module B is discarded, and the two cables, one exiting from each arm of the frame, now only carry power from a battery, located now where module B was before, allowing for a lighter and smaller module B, and lighter and thinner cables exiting from the frame of the device.

Example 9: Multimedia System with Smart Glasses with External Power Supply and Nothing Carried on the Waist Having the same general features as described in Example 8, the battery is substituted by another power source such as an electrical plug or generator, indefinitely extending the normal autonomy of the device, as long as power is available at the source, eliminating the need of the module B completely.

Example 10: Multimedia System with Smart Glasses that have the Microphone Near the Mouth Having the same general features as described in Example 6, the microphone is positioned near the mouth, mounted on an adjustable and detachable beam, allowing for better quality voice capture for recording and recognition, but with the disadvantage of being incompatible with some kinds of masks and other facial protections the user may be required to use.

Example 10: Multimedia System with Smart Glasses that Use an Earphone Instead of a BCT Having the same general features as described in Example 6, the BCT is replaced with an earphone, to adjust to situations where a free auditory canal isn't critical in the user's work.

Example 11: Multimedia System with Smart Glasses with No Optical Zoom

Having the same general features as described in Example 6, the optical mechanism is non-existent, so the focusing angle of the light of the LED is fixed and any camera zoom operation is done digitally.

Example 11: Multimedia System with Smart Glasses that have Anti-Fog Eyesight Correction Lenses Having the same general features as described in Example 6, any eyesight correction is to be employed with the anti-fog lenses, instead of the protection lenses.

Example 12: Multimedia System with Smart Glasses that Only have Vertical Motorization of the Camera and LED Platform Having the same general features as described in Example 6, the motorized system behind the camera and led platform, can only rotate the platform vertically.

Example 13: Multimedia System with Smart Glasses that Only have Horizontal Motorization of the Camera and LED Platform Having the same general features as described in Example 6, the motorized system behind the camera and led platform, can only rotate the platform horizontally.

The invention claimed is:

1. A multimedia system for acquisition, registration and multimedia management comprising at least one data acquisition module (A), for multimedia data acquisition, at least one computerized module (B), comprising a data processing unit for controlling the functions, recording, storing, managing and/or sharing, transmitting and/or streaming of multimedia data acquired by at least a module (A) and, at least one connection module (C1) for connecting the multimedia data acquisition module (A) to the computerized module (B) and/or to at least one multimedia data processing module (D), and/or to at least one peripheral device (P), wherein:

The data acquisition module (A) is a multimedia glasses device comprising:
- a frame (1) and lenses (10, 11),
- a camera (6) able to capture static and/or dynamic images, having a recognition of different recording modes, said camera (6) is attached to at least a motor (8) allowing the camera to change its angle relative to the glasses frame (1) and lenses (10, 11), and to change its point of view to match the user's point of view, signalling the beginning, stopping, and restarting motion picture capture, still image capture (photography) or adding bookmarks through audio feedback in response to actuation of a gesture- or voice-command of the user;
- an optical mechanism capable of changing the focusing angle of the light from the light signalling device and capable of zooming in and out the camera's field of view;
- an audio system comprising a microphone and speaker of the type bone conducting transducer (2) for capturing the user's voice, allowing said user to interact with the smart glasses device via computerized module (B) by giving instructions regarding the recording position, such as starting and stopping the recording mode, turning in and turning off the lightning device that signals the point of view of the camera, and adding voice highlights to the video, and where the speaker gives a feedback from the computerized module (B) to the user following an instruction given via the microphone and confirms which command will be executed afterwards;
- at least an inertial sensor to identify the position of the user's head, allowing to switch automatically between the available modes of the glasses;
- a first lighting device (5) for signalling the recording status of a camera (6) and a second lighting device for identification of the point of view of the recording,
- a connection module (C1); and A computerized module (B) comprising a data processing unit for controlling the functions, recording, storing, managing and/or sharing, transmitting and/or streaming the data acquired by a data acquisition module (A), wherein said module (B)
- is capable of reacting to the instructions provided by the user, via data acquisition module (A) and/or via its own touch screen and/or keyboard and can be controlled remotely by an authenticated person via a network; and
- of controlling the functions of at least one data acquisition module (A), in particular, to start, stop and restart of motion picture capture, still image capture (photography) or bookmarking of points of interest; and said module (B) further comprises:
- a computer vision algorithm for facial detection system, with the function of preventing or blocking the identification of people, in order to avoid capturing sensitive data related to identifiable people and covers the detected faces in real-time, before the record is made;
- has at least one connection module (C1), for connecting said computerized module (B) to the multimedia data acquisition module (A), a connection module (C2), for connecting the computerized module (B) to at least one multimedia data processing module (D), and/or to at least one peripheral device (P).

2. A multimedia system according to claim 1 further comprising at least one multimedia data processing module (D) for storing, recording, processing, editing, managing and/or sharing, transmitting and/or streaming multimedia data.

3. A multimedia system according to claim 2, wherein the processing module (D) comprises a data processing unit for storing, recording, processing, editing, managing and/or sharing, transmitting and/or streaming multimedia data, and at least a connection module (C2) for connecting said multimedia data processing module (D) to a at least one computerized module (B) and/or at least one connection module (C3) for connecting said processing module (D) to at least one peripheral device (P) and a computer program for performing a method of acquisition, registration and/or multimedia management comprising the following steps:
  a) Acquisition of multimedia data from at least one data acquisition module (A),
  b) Sending, transmitting and/or streaming the data acquired by at least one module (A) to at least one computerized module (B) through a connection module (C1),
  c) Sending, sharing, transmitting and/or streaming the data from at least one computerized module (B) to at least one processing module (D), through a connection module (C2),
  d) Storing, registering, processing, editing and/or managing received multimedia data in at least one processing module (D) and/or a data storage unit such as a floppy disk, a DVD, a Blu-Ray, a CD, a ROM, a PROM, an EPROM, an EEPROM or a FLASH memory having electronically readable control signals, which are capable of cooperating with a programmable computer system,
  e) Optionally sharing, transmitting and/or streaming said multimedia data to at least one peripheral device (P) through a connection module (C3) and/or to at least one other processing module (D),
  f) Optionally creating a multimedia data library (ML).

4. A multimedia system according to claim 3, wherein the processing module (D) comprises multimedia library (ML) having multimedia data recorded on a data storage unit such as a floppy disk, a DVD, a Blu-Ray, a CD, a ROM, a PROM, an EPROM, an EEPROM or FLASH memory, having electronically readable control signals, which are capable of cooperating with a programmable computer system and/or multimedia data processor, having these multimedia data been preferably obtained from recording multimedia events by at least a multimedia data acquisition module (A), preferably the multimedia glasses of the present invention.

5. A multimedia system according to claim 1 further comprising at least one peripheral device (P).

6. A multimedia system according to claim 1, wherein module (A) comprises a system for removal and replacement of the lenses.

7. A multimedia system according to claim 1, wherein module (A) comprises a water resistant or a water barrier coating.

8. A multimedia system according to claim 1, wherein module (A) comprises an anti-fog mechanism having inner lenses mounted behind the protection lenses of the glasses, with a thin layer of air contained between the protection lenses and the anti-fog lenses, using an adhesive material on the edge of the anti-fog lenses.

9. A multimedia system according to claim 1, wherein the connection module (C1) between module (A) and module (B) is a Y-cable connection.

10. A multimedia system according to claim 1, wherein the computerized module (B) is portable or transportable comprising an autonomous source of energy.

11. A multimedia system according to claim 10, wherein the power source is a battery.

12. A multimedia system according to claim 1, wherein the computerized module (B) comprises a touch screen.

13. A method of acquisition, registration and multimedia management comprising the following steps:
  a) Acquisition of multimedia data from at least one module (A) of the type multimedia glasses, which is controlled by at least one computerized module (B), wherein at least one module (A) includes:
    a frame (1) and lenses (10, 11),
    a camera (6) able to capture static and/or dynamic images, having a recognition of different recording modes, said camera (6) is attached to at least a motor (8) allowing the camera to change its angle relative to the glasses frame (1) and lenses (10, 11), and to change its point of view to match the user's point of view, signalling the beginning, stopping, and restarting motion picture capture, still image capture (photography) or adding bookmarks through audio feedback in response to actuation of a gesture- or voice-command of the user;
    an optical mechanism capable of changing the focusing angle of the light from the light signalling device and capable of zooming in and out the camera's field of view;
    an audio system comprising a microphone and speaker of the type bone conducting transducer (2) for capturing the user's voice, allowing said user to interact with the smart glasses device via computerized module (B) by giving instructions regarding the recording position, such as starting and stopping the recording mode, turning in and turning off the lightning device that signals the point of view of the camera, and adding voice highlights to the video, and where the speaker gives a feedback from the computerized module (B) to the user following an instruction given via the microphone and confirms which command will be executed afterwards;
    at least an inertial sensor to identify the position of the user's head, allowing to switch automatically between the available modes of the glasses;
    a first lighting device (5) for signalling the recording status of a camera (6) and a second lighting device for identification of the point of view of the recording,
  b) Sending, transmitting and/or streaming, the data, whereby the data acquired by at least one module (A) to at least one computerized module (B) through at least a connection module (C1),
  c) Optionally sending, sharing, transmitting and/or streaming the data, whereby the data is acquired from at least one computerized module (B) to at least one processing module (D), via at least one connection module (C2),
  d) registering, processing, editing and/or managing received multimedia data in at least one processing module (D) and/or a data storage unit such as a floppy disk, a DVD, a Blu-Ray, a CD, a ROM, a PROM, an EPROM, an EEPROM or a FLASH memory having electronically readable control signals, which are capable of cooperating with a programmable computer system, e) Optionally sharing, transmitting and/or streaming said multimedia data from at least one module (D) to at least one peripheral device (P) and/or to at least one other processing module (D) through a connection module (C3), f) creating a multimedia library (ML).

14. A method according to claim 13 wherein the multimedia library (ML) of step (f) has restricted access and is in digital format.

15. A multimedia glasses device (A) comprising a frame (1) and lenses (10, 11), a camera (6) able to capture static and/or dynamic images, having a recognition of different recording modes, said camera (6) is attached to at least a motor (8) allowing the camera to change its angle relative to the glasses frame (1) and lenses (10, 11), and to change its point of view to match the user's point of view, signalling the beginning, stopping, and restarting motion picture capture, still image capture (photography) or adding bookmarks through audio feedback in response to actuation of a gesture- or voice-command of the user;

an optical mechanism capable of changing the focusing angle of the light from the light signalling device and capable of zooming in and out the camera's field of view;

an audio system comprising a microphone and speaker of the type bone conducting transducer (2) for capturing the user's voice, allowing said user to interact with the smart glasses device via computerized module (B) by giving instructions regarding the recording position, such as starting and stopping the recording mode, turning in and turning off the lightning device that signals the point of view of the camera, and adding voice highlights to the video, and where the speaker gives a feedback from the computerized module (B) to the user following an instruction given via the microphone and confirms which command will be executed afterwards;

at least an inertial sensor to identify the position of the user's head, allowing to switch automatically between the available modes of the glasses;

a first lighting device (5) for signalling the recording status of a camera (6) and a second lighting device for identification of the point of view of the recording, and a connection module (C1).

\* \* \* \* \*